(12) United States Patent
Davis

(10) Patent No.: US 7,087,809 B2
(45) Date of Patent: Aug. 8, 2006

(54) NATURAL HERBICIDE RESISTANCE IN WHEAT

(75) Inventor: William H. Davis, Plainview, TX (US)

(73) Assignee: Natural Genes, Inc., Plainview, TX (US)

(*) Notice: Subject to any disclaimer, the term of this patent is extended or adjusted under 35 U.S.C. 154(b) by 76 days.

(21) Appl. No.: 10/714,957

(22) Filed: Nov. 18, 2003

(65) Prior Publication Data

US 2005/0108798 A1    May 19, 2005

(51) Int. Cl.
*A01H 5/10* (2006.01)
*A01H 1/00* (2006.01)
*A01H 4/00* (2006.01)

(52) U.S. Cl. .................. 800/276; 800/320.3

(58) Field of Classification Search ............ 800/260, 800/265, 266, 276, 320.3
See application file for complete search history.

(56) References Cited

U.S. PATENT DOCUMENTS

| | | | |
|---|---|---|---|
| 4,971,908 A | 11/1990 | Kishore et al. | |
| 5,145,783 A | 9/1992 | Kishore et al. | |
| 5,312,910 A | 5/1994 | Kishore et al. | |
| 5,352,605 A | 10/1994 | Fraley et al. | |
| 5,369,022 A * | 11/1994 | Newhouse et al. | 800/268 |
| 5,530,196 A | 6/1996 | Fraley et al. | |
| 5,633,435 A | 5/1997 | Barry et al. | |
| 5,858,742 A | 1/1999 | Fraley et al. | |
| 6,225,114 B1 | 5/2001 | Eichholtz et al. | |
| 6,248,876 B1 | 6/2001 | Barry et al. | |
| 6,339,184 B1 * | 1/2002 | Smith | 800/276 |
| 6,639,124 B1 | 10/2003 | Davis | |

OTHER PUBLICATIONS

Sebastian et al. 1987. Crop Sci. 27: 948-952.*

* cited by examiner

*Primary Examiner*—David H. Kruse
*Assistant Examiner*—Keith O. Robinson
(74) *Attorney, Agent, or Firm*—Buchanan Ingersoll PC

(57) ABSTRACT

The invention provides a process for selecting wheat plants and generating wheat lines which exhibit genetically-controlled glyphosate herbicide resistance in the absence of genetic engineering, wheat plants that are glyphosate herbicide resistant, and the naturally-occurring genes that confer glyphosate herbicide resistance exposed by the selection process. The process allows for the identification of wheat germplasm that contains natural glyphosate herbicide resistance genes and for directly isolating individual herbicide resistant plants from that germplasm. Such glyphosate herbicide resistance is genetically-controlled and can be reliably expressed and transferred to other wheat plants by conventional plant breeding methods. In addition the genes that control the herbicide resistance that are identified can be isolated for biotechnological applications to generate glyphosate herbicide resistance in wheat plants that do not contain the natural glyphosate herbicide resistance genes within their germplasm.

8 Claims, No Drawings

US 7,087,809 B2

NATURAL HERBICIDE RESISTANCE IN WHEAT

FIELD OF THE INVENTION

The invention provides a process for selecting wheat (i.e., *Triticum aestivum*) plants and generating wheat plants that exhibit genetically-controlled glyphosate herbicide resistance in the absence of genetic engineering, wheat plants that are glyphosate herbicide resistant due to the expression of naturally-occurring genes that are exposed by the aforementioned selection process, and the use of the glyphosate herbicide resistance genes through genetic engineering to confer glyphosate herbicide resistance to wheat plants that are naturally sensitive to exposure to glyphosate herbicide.

BACKGROUND OF THE INVENTION

Wheat long has been recognized to be an important crop, and is grown as a staple food crop in many parts of the world. This plant is grown primarily for the seed produced, although other parts of the plant have some commercial value. The seeds may be used for planting or as a source of food for human or livestock consumption.

Modern agriculture practices are increasingly taking advantage of herbicides to eliminate unwanted weeds from wheat fields and to minimize the expense of tilling fields to remove unwanted weeds. Presently, there are a limited number of marginally effective herbicides to kill unwanted plants on contact (post-emergent herbicides) that can be used in wheat without excessive crop injury. Such herbicides heretofore proposed for use with wheat have tended to be rather costly and are selective in their activity with the killing of only certain weeds.

The herbicide, glyphosate, is recognized to be an effective non-selective post-emergent herbicide. Plant transformation/genetic engineering has been used to modify other species of crop plants to incorporate resistance to the herbicidal effects of glyphosate. This method could also be used to modify wheat plants. Such genetic engineering/plant transformation involves the incorporation of a gene for herbicide resistance into the chromosome of the plant. Such procedures require special expertise and commonly are costly and as yet genetically-engineered glyphosate tolerant wheat plants are not commercially available. The resistance gene is part of a construct that is placed in the plant to impart resistance. In addition, the construct contains promoters that are responsible for activating the gene in select portions or in all parts of the plant. The presence or absence of these promoters is used to determine if the plant is the result of genetic engineering/plant transformation. The gene construct that is in commercially available crop plants includes the promoters, CaMV35S, enhanced CaMV35S, rice actin 1 promoter, 4-AS 1 (single CaMV35S plus four repeats of activating sequence), PCSLV, FMV35S, and NOS. Representative prior publications that concern the use of genetic engineering to produce such herbicide resistance include U.S. Pat. Nos. 4,971,908; 5,145,783; 5,312,910; 5,352,605; 5,530,196; 5,858,742; 6,248,876; and 6,225,114.

Naturally-occurring herbicide resistance in cotton plants is discussed in Applicant's copending U.S. patent application Ser. No. 09/782,191, filed Feb. 14, 2001 (now U.S. Pat. No. 6,639,124, granted Oct. 28, 2003), and naturally-occurring herbicide resistance in soybean plants is discussed in Applicant's copending U.S. patent application Ser. No. 10/119,194, filed Apr. 10, 2002 (now U.S. Pat. No. 6,927,319, granted Aug. 9, 2005).

It is an objective of the present invention is to provide a new route for providing genetically-controlled herbicide resistance in wheat plants in the absence of genetic engineering involving the insertion of a foreign gene into the wheat plants.

It is an object of the present invention to provide a wheat seed capable of forming a wheat plant having genetically-controlled glyphosate herbicide resistance that is not attributable to genetic engineering involving the insertion of a foreign gene into the wheat plants.

It is an object of the present invention to provide a wheat plant having genetically-controlled glyphosate herbicide resistance that is not attributable to genetic engineering involving the insertion of a foreign gene into the wheat plants.

It is another object of the present invention to provide a new isolated nucleic acid encoding for a protein which when expressed causes glyphosate herbicide resistance that is naturally-occurring in wheat.

It is another object of the present invention to provide an isolated nucleic acid comprising the $ng^{w1}ng^{w1}$ and $ng^{w2}ng^{w2}$ genes selected from 'W2-1' wheat having ATCC Accession No. PTA-7044 which causes a wheat plant to be glyphosate herbicide resistant, as well as to provide a vector and plant cell comprising the same.

It is a further object of the present invention to provide a wheat plant having genetically-controlled glyphosate herbicide resistance that can be sprayed with a herbicide during all phases of the life cycle of the plant without any substantial harm.

These and other objects, as well as the scope, nature and utilization of the claimed invention will be apparent to those skilled in this area of technology from the following detailed description and appended claims.

SUMMARY OF THE INVENTION

A process is provided for selecting a wheat plant which exhibits genetically-controlled herbicide resistance that is not attributable to genetic engineering comprising:
(a) soaking mature wheat seeds that are not genetically engineered for herbicide resistance in a liquid comprising glyphosate herbicide for a period of time sufficient for the glyphosate herbicide to reach the embryos of the wheat seeds,
(b) planting the wheat seeds following the soaking of step (a) in a growing medium and producing at least one wheat plant, and
(c) selecting a wheat plant from step (b) or from a subsequent generation that is produced following self-pollination which exhibits genetically-controlled glyphosate herbicide resistance that is not attributable to a foreign gene for herbicide resistance introduced by genetic engineering.

A *Triticum aestivium* plant is provided which exhibits genetically-controlled glyphosate herbicide resistance that is attributable to a combination the $ng^{w1}g^{w1}$ gene pair obtainable from the 'WA7824' wheat variety and the $ng^{w2}ng^{w2}$ gene pair obtainable from the 'Zeke' wheat variety.

A *Triticum aestivium* seed is provided which upon germination is capable of forming a wheat plant that exhibits genetically-controlled glyphosate herbicide resistance attributable to a combined presence of the $ng^{w1}ng^{w1}$ gene pair obtainable from the 'WA7824' wheat variety and the $ng^{w2}ng^{w2}$ gene pair obtainable from the 'Zeke' wheat variety.

A *Triticum aestivium plant* is provided which exhibits genetically-controlled glyphosate herbicide resistance that is attributable to the combined presence of the $ng^{w1}ng^{w1}$ gene pair and the $ng^{w2}$ $ng^{w2}$ gene pair obtainable from 'W2-1' wheat having ATCC Accession No. PTA-7044.

A *Triticum aestivium* seed is provided which upon germination is capable of forming a wheat plant that exhibits genetically-controlled glyphosate herbicide resistance that is attributable to the combined presence of the $ng^{w1}ng^{w1}$ gene pair and the $ng^{w2}$ $ng^{w2}$ gene pair obtainable from 'W2-1' wheat having ATCC Accession No. PTO-7044.

An isolated nucleic acid is provided which when expressed in a *Triticum aestivium* plant causes resistance to glyphosate herbicide comprising the combined presence of $ng^{w1}ng^{w1}$ gene pair obtainable from the 'WA7824' wheat variety and the $ng^{w2}$ $ng^{w2}$ gene pair obtainable from the 'Zeke' wheat variety.

An isolated nucleic acid is provided comprising the combined presence of the $ng^{w1}ng^{w1}$ gene pair and the $ng^{w2}ng^{w2}$ gene pair obtainable from 'W2-1' wheat having ATCC Accession No. PTA-7044 wherein said nucleic acid when expressed in *Triticum aestivium* causes said wheat plant to be glyphosate herbicide resistant.

DESCRIPTION OF THE PREFERRED EMBODIMENTS

At the present time fully effective herbicide resistance is not available to wheat growers. Glyphosate resistance in wheat would be a valuable addition and could be achieved using genetic engineering. However, public resistance to genetically-modified organisms (GMOs) has prevented the commercialization of GMO wheat. Resistance to glyphosate has been achieved by the introduction of bacterial genes into wheat germplasm that either code for target enzymes that are not affected by the herbicide (e.g., CP4 5-enolpyruvylshikimate-3-phosphate synthase (ESPS) from *Agrobacterium tumefaciens*) or for enzymes that break down the herbicide into an inactive form (e.g., glyphosate oxidase, gox gene, from *Ochrobacterium anthropi*) as reported by Zhou et al. (Plant Cell Reports 15:159–163, 1995) and in U.S. Pat. No. 6,153,812. Resistance to glyphosate herbicide could also be achieved by the introduction of an in vitro modified endogenous wheat (or other plant) ESPS gene, mutated to be insensitive to glyphosate inactivation back into the wheat genome as described in U.S. Pat. No. 6,225,114. Such genes have been constructed and introduced into wheat using now standard techniques of gene construction and plant transformation. The genes are engineered to function in a plant cell and are placed under the control of a promoter element, commonly derived from a plant viral genome (but there are others) that allows for the constitutive expression of the herbicide resistant or degradative enzyme. Such biotechnological strategies demand a lengthy and expensive research and development program. The present invention provides a method by which naturally-occurring plant genes that confer glyphosate herbicide resistance and that are already in wheat germplasm stocks are revealed, identified and exploited for commercial use in both conventional and biotechnological breeding programs.

The wheat seeds that are used as the starting material in the process of the present invention are harvested from wheat plants which have not been previously rendered glyphosate herbicide resistant by the use of genetic engineering through the insertion of a foreign gene for herbicide resistance. In preferred embodiments, the wheat seeds are derived from wheat plants of preexisting wheat varieties or lines which are recognized to display superior agronomic characteristics under conventional wheat growing conditions. For instance, known and publically-available hard red spring wheat varieties having good agronomic traits can be utilized. In a preferred embodiment the starting material possesses the 'WA7824' and 'Zeke' wheat varieties in its ancestory. The 'WA7824' wheat variety has been found to possess the $ng^{w1}ng^{w1}$ gene pair, and the 'Zeke' wheat variety has been found to possess the $ng^{w2}ng^{w2}$ gene pair. These genes in combination have been found to confer glyphosate herbicide resistance in wheat. The process of the present invention can be used to reveal and to obtain the same or similar naturally-occurring genes for glyphosate herbicide resistance present from among a myriad of *Triticum aestivium* sources that are available to plant scientists.

In the initial step of the process of the present invention mature wheat seeds that are not genetically engineered for herbicide resistance are soaked in a liquid comprising glyphosate herbicide for a period of time for the glyphosate herbicide to reach the embryos of the wheat seeds. Commonly the herbicide is present in a concentration that would be sufficient to kill wheat plants as well as weeds upon contact that commonly occur in wheat fields.

The glyphosate herbicide is N-(phosphonomethyl)glycine of the chemical formula:

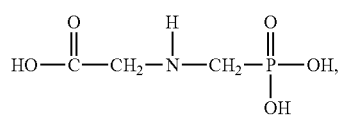

and is commercially available from Monsanto Corporation under the ROUNDUP trademark and other companies under various trademarks. This herbicide is a non-selective, broad spectrum, post-emergence herbicide that is registered for use in more than fifty crops. This molecule is an acid, which dissociates in aqueous solution to form phytotoxic anions. Several anionic forms are known. As used herein, the name "glyphosate" refers to the acid and its anions. Glyphosate inhibits the shikimic acid pathway that provides a precursor for the synthesis of aromatic amino acids. Specifically, glyphosate curbs the conversion of phosphoenolpyruvate and 3-phosphoshikimic acid to 5-enolpyruvyl-3-phosphoshikimic acid by inhibiting the enzyme 5-enolpyruvyl-3-phosphoshikimiate synthase.

Preferably the wheat seeds are soaked in an aqueous solution of the herbicide. Commonly the herbicide is present in the solution in a concentration of approximately 1.5 to 6 percent by weight, and most preferably in a concentration of approximately 2 percent by weight. Commonly the wheat seeds are simply immersed in the liquid comprising the herbicide. The soaking of wheat seeds is conducted for a period of time that is sufficient for the herbicide to reach the embryos of the wheat seeds. A soaking time of at least 6 hours has been found to yield good results. The liquid comprising the herbicide can be simply provided at room temperature when the wheat seeds are in contact with the liquid and are undergoing such soaking.

Following soaking in the herbicide, the resulting seeds are planted in a growing medium and germination of the seeds is attempted to produce wheat plants that display herbicide resistance. The herbicide resistance can be confirmed by spraying the resulting wheat plants with the glyphosate herbicide in a concentration typically used to kill weeds commonly encountered in a wheat field.

Alternatively, such screening of the resulting wheat plants for herbicide resistance can include the presence of the herbicide in the growing medium where the resulting seeds are planted. Good results are obtained in a preferred embodiment when one gallon of a solution containing the herbicide in a concentration of approximately 1.5 to 6 percent by weight is added to each 4 gallons of soil. The presence of the herbicide in the soil helps to assure that an atypical wheat seed having a harder seed coat has not given a false indication of herbicide resistance by its survival up to the point of germination. It has been found that a small proportion of the seeds following soaking in a liquid comprising a herbicide, and planting in a growth medium, will germinate and yield wheat plants that exhibit resistance to the herbicide.

The percentage of the plants that will grow normally following such seed treatments has been found to vary from variety to variety. Some varieties have produced no surviving plants in tests to date. Some varieties have produced up to approximately 4 surviving plant per 5,000 seeds, others approximately 1 surviving plant per 5,000 seeds. The herbicide resistance of the resulting plants can be further confirmed by another contact (e.g., spraying) with the glyphosate herbicide.

A portion of the herbicide-resistant wheat plant produced following such germination or a descendant thereof is analyzed to confirm that the manifest herbicide resistance is not the result of genetic engineering. This preferably is done by checking for the presence of a promoter or genetic marker sequences that were introduced by man when inserting a foreign gene construct for herbicide resistance into wheat germplasm. This analysis is used to confirm that the subject wheat plant is not a genetically modified organism and that the manifest herbicide resistance is attributable to a naturally-occurring genetic basis other than that introduced by genetic engineering. More specifically, this analysis is used to confirm that the resulting herbicide-resistant wheat plant or plants were not derived in some manner (e.g., by outcrossing) from a wheat plant that has been genetically engineered for herbicide resistance.

In accordance with the process of the present invention a wheat plant is next selected in which the herbicide resistance is under genetic control and in which there is no evidence of the use of genetic engineering to produce the herbicide resistance. Any suitable technique can be utilized to confirm the absence of the use of genetic engineering to produce the herbicide resistance. For instance, a DNA-polymerase chain reaction can be utilized. In a preferred embodiment a DNA-polymerase chain reaction is carried out on a portion of a wheat plant leaf. This analysis can be carried out to advantage when analyzing a portion of a young growing leaf. A DNA sequence analysis can be utilized to confirm that the gene for herbicide resistance does not conform to the sequence of a foreign gene inserted into the wheat genome by genetic engineering. At this time the DNA sequences that are relevant are those that are in common use in commercially grown transgenic crops. The sequences that are in use and are detectable by PCR screening are the sequences for the cauliflower mosaic viral 35S promoter, the individual coding sequences that encode proteins that when expressed render the plant tolerant to a particular herbicide, e.g., the CP4 EPSPS gene from *Agrobacterium* enabling resistance to glyphosate, and the chimeric NOS-NPTII-NOS gene for kanamycin resistance. The presence and expression of the CP4 EPSPS gene conferring glyphosate resistance can also be detected by use of a specific antibody directed against the protein encoded by this gene. A simple field kit for detecting GMO herbicide resistance is available from the AIT Company of Iroquis, South Dakota, as well as other sources.

Also, contemplated by the instant invention are the nucleic acids which comprise the genes which when expressed in the wheat plant provide herbicide resistance in wheat plants. Once a wheat plant which exhibits genetically-controlled herbicide resistance that is not attributable to genetic engineering has been identified, the gene responsible for said naturally-occurring herbicide resistance can be genetically mapped, identified, isolated, and the sequence determined by anyone competent in the art. See, *Plant Genomes: Methods for Genetic and Physical Mapping*, J. S. Beckmann and T. C. Osborn, 1992, Kluwer Academic Publishers; *Genome Mapping in Plants*, A. Paterson (1996) Harcourt Brace and Co.; *Wheat Genome Mapping*, A. Kalinski (1996) Diane Publishing Co.; and *Methods in Molecular Biology*, Vol. 82, *Arabidopsis Protocols*, J. M. Martinez Zapater and J. Salinas (1998) Humana Press. The then isolated nucleic acid encoding the gene conferring the naturally-occurring herbicide resistance encodes a protein responsible for causing the plant to be herbicide resistant. This isolated nucleic acid can then be used to (1) identify other nucleic acids which may contain naturally-occurring mutations that provide herbicide resistance to wheat plants; (2) introduce the isolated nucleic acid into a wheat plant which lacks herbicide resistance by means of genetic engineering which are known to the artisan of ordinary skill; (3) insert the isolated nucleic acid into a suitable vector which can be expressed in a wheat plant; and (4) insert the vector into a plant cell (e.g., a wheat plant cell).

The present invention also contemplates the fabrication of DNA constructs comprising the isolated nucleic acid sequence containing the coding sequence from the gene that confers herbicide resistance operatively linked to plant gene expression control sequences. "DNA constructs" are defined herein to be constructed (not naturally-occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., *Molecular Cloning: A Laboratory Manual*, Cold Spring Harbor, N.Y. (1982), and Sambrook et al., *Molecular Cloning: A Laboratory Manual*, Cold Spring Harbor, N.Y. (1989).

"Expression control sequences" are DNA sequences involved in any way in the control of transcription or translation. Suitable expression control sequences and methods of making and using them are well known in the art.

The expression control sequences must include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, *Nucleic Acids Res.*, 15, 2343–2361 (1987). Also, the location of the promoter relative to the transcription start may be optimized. See, e.g., Roberts et al., *Proc. Natl. Acad. Sci. USA*, 76, 760–764 (1979). Many suitable promoters for use in plants are well known in the art.

For instance, suitable constitutive promoters for use in plants include the promoters of plant viruses, such as the peanut chlorotic streak caulimovirus (PC1SV) promoter (U.S. Pat. No. 5,850,019); the 35S and 19S promoter from cauliflower mosaic virus (CaMV) (Odell et al., 1313:3810–812, 1985); promoters of the *Chlorella* virus methyltransferase genes (U.S. Pat. No. 5,563,328); the full-length transcript promoter from figwort mosaic virus (FMV) (U.S. Pat. No. 5,378,619); the promoters from such genes as rice actin (McElroy et al., *Plant Cell* 2:163–171 (1990)), ubiquitin (Christiansen et al., *Plant Mol. Biol.* 12:619–632 (1989)), and (Christiansen et al., *Plant Mol. Biol.* 18: 675–689 (1992)), pEMU (Last et al., *Theor. Appl. Genet.* 81:581–588 (1991)), MAS (Velten et al., *Embo J.* 3:2723–2730 (1984)), wheat H# histone (Lepetit et al., *Mol. Gen. Genet.* 231:276–285 (1992), and Atanassova et al., *Plant Journal* 2:29 1–300 (1992)), *Brassica napus* ALS3 (International Publication No. WO 97/41228); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al., *PNAS* 90:4567–4571 (1993)): the promoter of the wheat In 2 gene which responds to benzenesulfonomide herbicide safeners (U.S. Pat. No. 5,364,780 and Gatz et al. *Mol. Gen. Genet.* 243:32–38 (1994)), and the promoter of the Tet repressor from Tn10 (Gatz et al. *Mol. Gen. Genet.* 227:229–237 (1991)). A particularly preferred promoter for use in plants is one that responds to an inducing agent to which plants normally do not respond. An exemplary inducible promoter of this type is the inducible promoter from a steroid hormone gene, the transcriptional activity of which is induced by a glucosteroid hormone (Schena et al., *PNAS* 88:10421 (1991)) or the recent application of a chimeric transcription activator, XVE, for use in an estrogen receptor-based inducible plant expression system activated by estradiol (Zou et al., *The Plant Journal* 24 265–273 (2000)). Other inducible promoters for use in plants are described in European Patent No. 332104, International Publication No. WO 93/21334 and International Publication No. WO 97/06269, and discussed in Gatz C, and Lenk I. (1998) *Trends in Plant Science*, 3, 352–358, and Zou J, and Chua N-H. (2000) *Curr. Opin. Biotechnol.*, 11, 146–151.

Finally, promoters composed of portions of other promoters and partially or totally synthetic promoters can be used. See, e.g., Ni et al., *Plant Journal* 7:661–676 (1995) and International Publication No. WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316), and the FMV enhancer element (Maiti et al., *Transgenic Research*, 6:143–156 (1997)). See also, International Publication No. WO 96/23898 and *Enhancers and Eukaryotic Expression* (Cold Spring Harbor Press, Cold Spring Harbor, N.Y., 1983).

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants and other eukaryotes. Suitable 3' untranslated sequences for use in plants include those of the cauliflower mosaic xvirus 35S gene, the phaseolin seed storage protein gene, the pea ribulose-1,5-bisphosphate carboxylase small subunit E9 gene, the wheat 7S storage protein gene, the octopine synthase gene, and the nopaline synthase gene.

A 5' untranslated leader sequence can also employed. The 5' untranslated leader sequence is the portion of an mRNA which extends from the 5' CAP site to the translation initiation codon. This region of the mRNA is necessary for translation initiation in plants and plays a role in the regulation of gene expression. Suitable 5' untranslated leader sequence for use in plants includes those of alfalfa mosaic virus, cucumber mosaic virus coat protein gene, and tobacco mosaic virus.

The DNA construct may be a vector. The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence encoding the herbicide resistance gene product. The vector desirably also has unique restriction sites for the insertion of DNA sequences. If a vector does not have unique restriction sites it may be modified to introduce or eliminate restriction sites to make it more suitable for further manipulation.

Vectors suitable for use in expressing the nucleic acids, which when expressed in a plant confer herbicide resistance, include but are not limited to pMON979, pMON977, pMON886, pCaMVCN, and vectors derived from the tumor inducing (Ti) plasmid of *Agrobacterium tumefaciens* described by Rogers et al., *Meth. Enzymol.*, 153:253–277 (1987). The nucleic acid is inserted into the vector such that it is operably linked to a suitable plant active promoter. Suitable plant active promoters for use with the nucleic acids include, but are not limited to CaMV35S, ACTJN, FMV35S, NOS and PCSLV promoters. The vectors comprising the nucleic acid can be inserted into a plant cell using a variety of known methods. For example, DNA transformation of plant cells include but are not limited to *Agrobacterium*-mediated plant transformation, protoplast transformation, electroporation, gene transfer into pollen, injection into reproductive organs, injection into immature embryos and particle bombardment. These methods are described more fully in U.S. Pat. No. 5,756,290, and in a particularly efficient protocol for wheat described in U.S. Pat. No. 6,153,812, and the references cited therein. Site-specific recombination systems can also be employed to reduce the copy number and random integration of the nucleic acid into the cotton plant genome. For example, the Cre/lox system can be used to immediate lox site-specific recombination in plant cells. This method can be found at least in Choi et al., *Nuc. Acids Res.* 28: B19 (2000).

The herbicide resistance that is revealed when practicing the present invention is an infrequent naturally-occurring genetic mutation and not the product of an introduced genetic modification. The process steps of the present invention have been found through empirical research to enable the isolation of such genetic mutants in wheat on a reliable basis. Such herbicide resistance is under genetic control through the expression of genes for herbicide resistance and can be readily transferred to other wheat varieties and lines, by conventional plant breeding techniques.

The herbicide resistance of the present invention can be provided in true-breeding wheat varieties and lines as well as in $F_1$ wheat hybrids. When forming $F_1$ hybrids, the requisite genetic control is provided in both parent plants (e.g., in cytoplasmic male sterile and in restorer parent plants). The techniques used in such a plant breeding program are commonly known to those familiar in plant science and are described, in part, in the treatise "Breeding Field Crops", 4th Edition (1995) by J. Poehlman and D. Sleper, published by Iowa State University Press, Ames, Iowa.

Herbicide resistant wheat plants of the present invention can be sprayed with herbicide at any stage of the plant life cycle without deleterious results. For instance, herbicide resistant wheat plants of the present invention can be treated with a herbicide from seed through flowering and during head formation and filling without injury. This is not always the case with genetically engineered herbicide resistance. A longer and safer period for spraying with a herbicide is provided by the present invention. Accordingly, a wheat grower when utilizing wheat plants of the present invention, can spray the wheat field with herbicide whenever the need for weed control is apparent without restriction with respect to timing. This provides greater weed control options and flexibility to the wheat grower.

In yet another embodiment, the invention provides a method of controlling weeds in a field where herbicide resistant plants of the present invention or transgenic plants utilizing nucleic acid sequences, constructs or vectors from the present invention are growing. The method comprises applying an effective amount of glyphosate herbicide to the field to control the weeds. The glyphosate herbicide is applied to the wheat field at a rate and amount suitable for effective weed control while maintaining the viability of the wheat plants. Methods of applying herbicides, including glyphosate, and the amounts of them that are effective to control various types of weeds are known. See, *Crop Protection Reference* (Chemical and Pharmaceutical Press, Inc., New York, N.Y., 11th edition 1995).

The following Examples are presented as specific illustrations of the claimed invention. It should be understood, however, that the invention is not limited to the specific details of the Examples.

Fifteen different known and publically available hard red spring wheat populations (W1 through W15) were chosen for evaluation and screening in accordance with the process of the present invention. Each of the starting materials was believed to lack herbicide resistance that is attributable to genetic engineering. Also, each population, as all other *Triticum aestivium* varieties, was regarded to be highly sensitive to glyphosate herbicide during previous observations. Each wheat population consisted of approximately 5,000 seeds and possessed the pedigree specified in Table I. A total of approximately 75,000 seeds were evaluated.

Individual batches of each wheat population were initially immersed and were soaked in 2 percent aqueous solutions of glyphosate herbicide that were present at room temperature. The wheat seeds were provided in contact with the glyphosate herbicide for a period of 6 hours during which time the glyphosate herbicide reached the embryos of the seeds.

Each wheat seed population was labeled and next was planted in a 50/50 sandy-loam top soil/peat growing medium. The wheat seeds were present in flats containing the growing medium at a depth of approximately 2 inches. The same 2 percent by weight aqueous solutions of glyphosate herbicide were poured into each growing medium containing the wheat seeds.

The flats containing the wheat seeds next were placed in a greenhouse under ambient conditions in an effort to achieve germination. The sandy-loam top soil/peat growing medium was periodically watered in an effort to achieve near field growing conditions except for the presence of glyphosate herbicide. Over the next 10 to 15 days the flats were observed in an effort to detect germination and the emergence of any seedlings.

The vast majority of the glyphosate herbicide-treated seeds failed to germinate. Of those that did germinate some died within the first 2 days, and only 6 of the 15 wheat populations produced any plants following the soaking in the glyphosate herbicide as reported in Table I. These 6 populations were W1 to W5 and W15. Each plant was carefully preserved and tagged in order to preserve the lineage for those that survived the exposure to the glyphosate herbicide at the seed stage.

Next a small portion of each surviving plant was DNA tested for the possible presence of transgenic elements to which the glyphosate herbicide resistance could be attributed. All of the 15 surviving wheat plants tested negative for transgenic elements in PCR-based tests. Accordingly, the glyphosate herbicide survival capability that was revealed by the foregoing exposure to the herbicide was deemed to be naturally-occurring.

TABLE I

| Wheat Population Designation | Parental Pedigree | Number of Surviving Wheat Plants |
|---|---|---|
| W1 | 'ID377'/'WestBred 926' | 4 |
| W2 | 'WA7824'/'Zeke' | 5 |
| W3 | 'SLW97606'/'WestBred 926' | 1 |
| W4 | 'SLW97606'/'WestBred 936' | 2 |
| W5 | 'SLW97606'/'Zeke' | 1 |
| W6 | 'BZ692-108b'/'Calorwa' | 0 |
| W7 | 'BZ966-472w'/'Pristine' | 0 |
| W8 | 'Hank'/'BZ994-484' | 0 |
| W9 | 'MT9959'/'Hank' | 0 |
| W10 | 'McNeal'/'Parshall' | 0 |
| W11 | 'Reeder'/'Conan' | 0 |
| W12 | 'WA7899'/'Jefferson' | 0 |
| W13 | 'Alpowa'/'Zak' | 0 |
| W14 | 'Vanna'/'Zak' | 0 |
| W15 | 'Zak'/'BZ698-41' | 4 |

The 17 surviving plants were allowed to grow to maturity, each underwent self-pollination, and the seeds of each head were separately harvested and were appropriately labeled. Surviving plants from Population W15 did not set seeds until approximately one month later than the other survivors and were not continued for further analysis.

Steps next were taken to further isolate the glyphosate herbicide resistance that had been previously revealed. Fifteen seeds from each head of each surviving plant were next planted in 64 individual flats in a greenhouse containing a like 50/50 sandy-loam top soil/peat growing medium. A designation system was adopted which began with the initial Wheat Population Designation (e.g., W1) next followed by the plant number (e.g., –1, –2 for W1), and finally followed by the head number (e.g., h1). The wheat plants of the 64 flats were identified as follows:
  (a) W1-1 h1 through h4,
  (b) W1-2 h1 through h3,
  (c) W2-1 h1 through h12,
  (d) W2-2 h1 through h8,
  (e) W2-3 h1 through h6,
  (f) W2-4 h1 through h10,
  (g) W5-2 h1 through h4,
  (h) W3-1 h1 through h4,
  (i) W4-1 h1 through h4,
  (h) W4-2 h1 through h3,
  (k) W4-3 h1 through h3, and
  (l) W5-1 h1 through h3.

The seeds were encouraged to germinate and wheat plants emerged. At the three-leaf stage a 1.2 percent aqueous solution of glyphosate herbicide was applied to the plants by spraying. Only a single seedling derived each of W1-2 and W2-4 survived this application of glyphosate herbicide. Remnant seeds from these 2 plants taken from heads W2-1-h10 and W2-4-h9 were planted in the greenhouse, germinated, and underwent self-pollination to increase the seeds. Plants derived from these seeds were not subjected to the glyphosate herbicide in an effort to maximize yield and to establish a germplasm base for further testing. W2-1-h10 produced six healthy plants that were designated W2-1-h10-p1-1a through -6a. The "a" designation served to specify that the generation was not treated with glyphosate herbicide. Similarly, W2-4-h9 produced 10 plants that were designated W2-4-h9-p1-1a through 10a. All plants were allowed to mature, to undergo self-pollination, and to produce seed heads. Each head was tagged to maintain a clear record of lineage. Seeds from each head were planted in separated rows (i.e., in head rows) in the field. The following 101 head rows were established:

W2-1-h10-p1-1a, h1 through h5,
W2-1-h10-p1-2a, h1 through h2,
W2-1-h10-p1-3a, h1 through h8,
W2-1-h10-p1-4a, h1 through h8,
W2-1-h10-p1-5a, h1 through h4,
W2-1-h10-p1-6a, h1 through h4,
W2-4-h9-p1-1a, h1 through h5,
W2-4-h9-p1-2a, h1 through h6,
W2-4-h9-p1-3a, h1 through h8,
W2-4-h9-p1-4a, h1 through h6,
W2-4-h9-p1-5a, h1 through h5,
W2-4-h9-p1-6a, h1 through h7,
W2-4-h9-p1-7a, hI through hi 1,
W2-4-h9-p1-8a, h1 through h6,
W2-4-h9-p1-9a, h1 through h6, and
W2-4-h9-p1-10a, h1 through h10.

The wheat seedlings arising from the germination of this planting were allowed to establish and grow to the three-leaf stage. At this stage of growth glyphosate herbicide was applied to the plants at a rate of 32 oz. per Acre. Survivors of this treatment were allowed to mature, to undergo self-pollination, and the heads from each plant were tagged, removed, and placed in individual containers to ensure a record of continuous lineage from the plants used in the increase (i.e., W2-1-h10-p1-1a through 6a and W2-4-h9-p1-1a through 10a). Seeds from each head removed from the surviving plants that were exposed to glyphosate herbicide in the field head row plots next were planted in flats in the greenhouse for germination and seedling establishment. The seeds from each head were planted in separate flats to maintain the integrity of each line. At the three-leaf stage, the resulting seedlings were sprayed with an aqueous 1.2 percent by weight solution of glyphosate herbicide. Surviving plants were allowed to grow to maturity, to undergo self-pollination, and to produce heads and seeds. This was done to ensure that the survivors of the glyphosate herbicide treatment also remained fertile and produced viable seeds. All selections generated plants that were tolerant to the herbicide; however, four selections were isolated where all of the plants that arose from the seeds taken from the heads isolated from the surviving plants that had been exposed to glyphosate herbicide in the head rows, survived the glyphosate herbicide treatment in the greenhouse and produced heads and seeds. The results from the glyphosate herbicide treatment of the four selections, grown in greenhouse flats are presented in Table II.

TABLE II

| Parental Pedigree | Selection | Number of Survivors of Glyphosate Herbicide Treatment | Number Killed by Glyphosate Herbicide Treatment |
|---|---|---|---|
| 'WA7824'/'Zeke' | W2-1-h10-p16a-h2-h5 | 15 | 0 |
| 'WA7824'/'Zeke' | W2-1-h10-p16a-h2-h1 | 10 | 0 |
| 'WA7824'/'Zeke' | W2-4-h9-p13a-h2-h17 | 3 | 0 |
| 'WA7824'/'Zeke' | W2-4-h9-p13a-h2-h18 | 5 | 0 |

All surviving plants were tested for genetic elements associated with the genetic engineering for glyphosate herbicide resistance by PCR based testing. None of the surviving plants contained the genetic elements associated with genetic engineering and were judged to be free of genetically-engineered glyphosate herbicide resistance. Accordingly, naturally-occurring glyphosate herbicide resistance was revealed. The 'WA7824' wheat variety supplied the $ng^{w1}ng^{w2}$ gene pair, and the 'Zeke' wheat variety supplied the $ng^{w2}ng^{w2}$ gene pair. These genes in combination conferred the glyphosate herbicide resistance that was observed. Such glyphosate herbicide resistance was under genetic control and was capable of being readily transferred to other wheat plants using conventional known plant breeding techniques. Additionally, the genes that control the herbicide resistance can be isolated using known techniques for use in biotechnological applications to generate glyphosate herbicide resistance in wheat plants that do not contain the natural glyphosate herbicide resistance genes within their germplasm.

2,500 wheat seeds derived from selection W2-1 (described above) were named 'W2-1', were increased by self-pollination, and were deposited on Sep. 23, 2005 under the terms of the Budapest Treaty at the American Type Culture Collection, 10801 University Boulevard, Manassas, Va. 20110-2209, U.S.A., and have received ATCC Accession No. PTA-7044. Seeds from this deposit will be irrevocably made available upon the grant of a patent that makes reference to this deposit. However, the availability of these seeds is not to be construed as a license to practice the claimed invention in contravention of rights granted under the authority of any government in accordance with its patent or breeder's right laws.

Seed increases from each of the following glyphosate tolerant wheat lines, W1-1-p11-h1-h2, W1-1-p11-h1-h4, W2-1-h10-p16a-h2-h5, W2-1-h10-p16a-h2-h5, W2-4-h9-p13a-h2-h17, W2-4-h9-p16a-h3-hl, W2-4-h9-p13a-h2-h3, W2-4-h9-p16a-h7-h3, W2-4-h9-p16a-h7-h6, W2-4-h9-p16a-h7-h9, W2-4-h9-p16a-h7-h12, W2-4-h9-p18a-h1-h2, W2-4-h9-p18a-h1-h10, W2-4-h9-p18a-h1-h12, W2-4-h9-p18a-h1-h15, W2-4-h9-p18a-h1-h16, W2-4-h9-p18a-h1-h19, W2-4-h9-p18a-h1-h20, W2-4-h9-p18a-h1-h21, W2-4-h9-p18a-h1-h23, W2-4-h9-p19a-h1-h1, W2-4-h9-p19a-h2-h1, W2-4-h9-p19a-h3-h1, W2-4-h9-p19a-h8-h5, W2-4-h9-p19a-h8-h3, W2-4-h9-p110a-h1-h2 were planted for two field trials; one in Montana and the other in Plainview Texas. Seed from surviving plants from the W1-1-p11-h1-h2, W2-4-h9-p16a-h7-h3, W2-4-h9-p18a-h1-h16, W2-4-h9-p18a-h1-h21, and W2-4-h9-p18a-h1-h23 lines, combining both herbicide tolerance and field performance, were collected for further breeding trials and for the generation of homozygous lines. The seed increase for the W2-1-h10-p16a-h2-h1 line remains to be subjected to field selection.

Although the invention has been described with reference to preferred embodiments, it is to be understood that variations and modifications may be resorted to as will be apparent to those skilled in the art. Such variations and modifications are to be considered with the purview of the claims appended hereto.

I claim:

1. A process is provided for selecting a whole plant which exhibits genetically-controlled naturally-occurring glyphosate herbicide resistance that is not attributable to genetic engineering consisting essentially of:
   (a) soaking mature wheat seeds that have not been mutagenized and are not genetically engineered for herbicide resistance in a liquid comprising glyphosate herbicide for a period of time sufficient for the glyphosate herbicide to reach the embryos of the wheat seeds,
   (b) planting the wheat seeds following the soaking of step (a) in a growing medium and producing at least one wheat plant, and
   (c) selecting a wheat plant from step (b) or from a subsequent generation that is produced following self-pollination which exhibits genetically-controlled naturally-occurring glyphosate herbicide resistance that is not attributable to a foreign gene for herbicide resistance introduced by genetic engineering.

2. The process according to claim 1 wherein said glyphosate herbicide in step (a) is provided in an aqueous solution in a concentration of approximately 1.5 to 6 percent by weight.

3. The process according to claim 1 wherein said glyphosate herbicide in step (a) is provided in an aqueous solution in a concentration of approximately 2 percent by weight.

4. The process according to claim 1 wherein said soaking of step (a) has a duration of at least 6 hours.

5. The process according to claim 1 wherein in step (b) said liquid comprising said glyphosate herbicide additionally is added to said growing medium.

6. The process according to claim 1 wherein said wheat plant that is selected in step (c) survives when sprayed with a liquid comprising said glyphosate herbicide in a concentration that commonly would kill a wheat plant.

7. The process according to claim 1 wherein said mature wheat seeds that are soaked in said glyphosate herbicide of step (a) are produced from the cross of the 'WA7824' and 'Zeke' wheat varieties.

8. The process according to claim 1 wherein said mature wheat seeds that are soaked in said glyphosate herbicide of step (a) include the 'WA7824' and 'Zeke' wheat varieties in their ancestry.

* * * * *

UNITED STATES PATENT AND TRADEMARK OFFICE
CERTIFICATE OF CORRECTION

PATENT NO. : 7,087,809 B2
APPLICATION NO. : 10/714957
DATED : August 8, 2006
INVENTOR(S) : William H. Davis It is certified that error appears in the above-identified patent and that said Letters Patent is hereby corrected as shown below:

In the Claims:
Col. 13, Line 8
Claim 1, line 1, before "plant", please delete "whole" and insert --wheat--.

Signed and Sealed this

Nineteenth Day of December, 2006

JON W. DUDAS
*Director of the United States Patent and Trademark Office*